(12) United States Patent
Niwa et al.

(10) Patent No.: US 7,445,793 B2
(45) Date of Patent: Nov. 4, 2008

(54) SUPPORT FOR TISSUE REGENERATION AND PROCESS FOR PRODUCING THE SAME

(75) Inventors: Hideo Niwa, Akashi (JP); Takeshi Fukuchi, Kobe (JP); Ichiro Shimizu, Osaka (JP); Masao Sato, Kobe (JP); Akiko Nishi, Akashi (JP); Kenji Yamashita, Takamatsu (JP); Tadashi Kaneko, Tokorozawa (JP); Hajime Ohgushi, Kashihara (JP); Koji Hattori, Kashihara (JP); Kota Uematsu, Kashihara (JP)

(73) Assignees: Kaneka Corporation, Osaka (JP); GC Corporation, Tokyo (JP); Natl. Inst. of Adv. Ind. Science & Tech., Tokyo (JP)

( * ) Notice: Subject to any disclaimer, the term of this patent is extended or adjusted under 35 U.S.C. 154(b) by 360 days.

(21) Appl. No.: 10/527,075

(22) PCT Filed: Sep. 9, 2003

(86) PCT No.: PCT/JP03/11471

§ 371 (c)(1),
(2), (4) Date: Nov. 7, 2005

(87) PCT Pub. No.: WO2004/035101

PCT Pub. Date: Apr. 29, 2004

(65) Prior Publication Data

US 2006/0127368 A1 Jun. 15, 2006

(30) Foreign Application Priority Data

Sep. 9, 2002 (JP) ............................. 2002-263126
Dec. 26, 2002 (JP) ............................. 2002-377780
Aug. 8, 2003 (JP) ............................. 2003-289744

(51) Int. Cl.
*A61F 2/02* (2006.01)
*A61F 2/00* (2006.01)
*A61F 2/28* (2006.01)
*A61K 9/14* (2006.01)
*A61K 48/00* (2006.01)

(52) U.S. Cl. ...................... 424/426; 424/423; 435/128; 435/129; 435/325; 435/396; 435/399; 435/435; 623/23.58; 623/23.75; 623/23.76

(58) Field of Classification Search ................ 435/128, 435/129, 435, 396, 399, 325; 424/423, 426; 623/23.58, 23.75, 23.76
See application file for complete search history.

(56) References Cited

U.S. PATENT DOCUMENTS

| | | | |
|---|---|---|---|
| 5,041,138 A | 8/1991 | Vacanti et al. | |
| 5,869,080 A | 2/1999 | McGregor et al. | |
| 5,891,455 A | 4/1999 | Sittinger et al. | |
| 6,103,255 A * | 8/2000 | Levene et al. | 424/426 |
| 6,337,198 B1 | 1/2002 | Levene et al. | |
| 6,534,084 B1 * | 3/2003 | Vyakarnam et al. | 424/443 |
| 6,562,374 B1 * | 5/2003 | Han et al. | 424/484 |
| 7,112,417 B2 * | 9/2006 | Vyakarnam et al. | 435/41 |
| 2003/0004578 A1 * | 1/2003 | Brown et al. | 623/23.72 |
| 2003/0049299 A1 * | 3/2003 | Malaviya et al. | 424/423 |
| 2003/0105525 A1 * | 6/2003 | Vyakamam et al. | 623/15.12 |
| 2004/0191292 A1 * | 9/2004 | Chou | 424/426 |

FOREIGN PATENT DOCUMENTS

| | | |
|---|---|---|
| EP | 0 747 068 A1 | 12/1996 |
| EP | 1 173 235 B1 | 1/2002 |
| EP | 1 234 587 A1 | 8/2002 |

(Continued)

OTHER PUBLICATIONS

International Search Report from Corresponding International Application No. PCT/JP03/11471, Dated Feb. 3, 2004, 2 pages.
English Translation of International Preliminary Examination Report, From Corresponding International Application No. PCT/JP03/11471, Dated Sep. 17, 2005, 7 pages.

*Primary Examiner*—Herbert J. Lilling
(74) *Attorney, Agent, or Firm*—Brinks Hofer Gilson & Lione

(57) ABSTRACT

The present invention provides a scaffold in which cells can be stably retained and grafted in a uniform distribution state in the culture, preferable proliferation ability and viability can be secured, and particularly in the case of cartilage, fixation treatment such as suture can be carried out in the transplantation into affected parts after the culture, and the mechanical strength is provided sustainable for (weighted) compression at the initial stage of transplantation.

The present invention relates to a 3-dimensional porous scaffold for tissue regeneration
 which comprises a structure composed of vertically long-shaped pores having a pore diameter of not less than 10 µm to not more than 500 µm and pore length of not less than 20 µm to not more than 1 cm being juxtaposedly arranged
 obtained by a production process comprising rapid freeze-drying as a key technology.

Further, the invention relates to the above 3-dimensional porous scaffold in which seeding properties of cells are improved by a pore enlargement treatment of one side face by a separation operation, a salt elution operation of a surface part, or a combination of these operations. It becomes possible to produce a 3-dimensional cell combination having excellent degree of tissue formation and medical treatment effect by seeding a cell or precursor cell derived from a tissue in this scaffold, and culturing them in an artificial environment and/or the living body.

4 Claims, 17 Drawing Sheets

| | FOREIGN PATENT DOCUMENTS | | |
|---|---|---|---|
| JP | 9-99051 A | 4/1997 | |
| JP | 2000-189510 A | 7/2000 | |
| JP | 2002-291867 A | 10/2002 | |
| JP | 2002-541925 A | 12/2002 | |
| WO | WO 90/12603 | 11/1990 | |
| WO | WO 94/20151 | 9/1994 | |
| WO | WO 95/33821 | 12/1995 | |
| WO | WO 97/30662 | 8/1997 | |
| WO | WO 00/62829 A1 | 10/2000 | |

\* cited by examiner

Fig. 16B

| | Seeded group | Scaffold group | Defect group |
|---|---|---|---|
| Appearance | | | |
| HE staining | | | |
| AB staining | | | |

SUPPORT FOR TISSUE REGENERATION AND PROCESS FOR PRODUCING THE SAME

RELATED APPLICATIONS

This application is a nationalization of PCT Application No. PCT/JP03/11471 filed Sep. 9, 2003. This application claims priority from Japanese Patent Application No. 2003-289744 filed on Aug. 8, 2003; Japanese Patent Application No. 2002-263126 filed on Sep. 9, 2002; and Japanese Patent Application No. 2002-377780 filed on Dec. 26, 2002.

TECHNICAL FIELD

The present invention relates to a 3-dimensional porous scaffold suited for regeneration of living tissues, the process for producing the same, and further a 3-dimensional cell combination using said scaffold and the process for producing the same.

BACKGROUND ART

Currently, tens of millions of people are receiving medical treatment of their tissue damages due to accidents or serious organ failures. However, the current surgical treatment or pharmaceutical treatment such as organ transplant cannot be said as a sufficient medical treatment in view of problems of organ supply or the effects of medicine itself, and the like. Thus, many researches have been conducted regarding regeneration of various living tissues which can be transplanted into such patients. Particularly as for the cartilage, it is supposed that there are millions of patients suffering from sports disorders, osteoarthritis or the like only within the country, and thus the development of a technology for enabling producing a cultured cartilage aiming for treating such disorder is strongly desired. The "cultured cartilage" as used herein refers to a 3-dimensional cell combination constituted from cartilage cells.

As regarding the production of a cultured cartilage, there have been reported the production example of a 3-dimensional carrier structure in an artificial environment such as a test tube or incubator by Minas et al., Sittinger, or Naughton et al., Minas et al., Articular Cartilage Defects, 1997, 20 volumes, No. 6, 525-538 pages; International Publication WO 94/20151; International Publication WO 95/3382 1), and the example of in vivo cartilage formation using a scaffold/cell mixture by Vacanti et al. or Naughton et al. (U.S. Patent No. 5,041,138; International Publication WO 90/12603; International Publication WO 97/30662).

In the production of a cultured cartilage, firstly, it is important to secure a scaffold having sufficient functions as a support to which cells are seeded and cultured, and a certain level of mechanical strength. That is, it is required to use a scaffold in which cells can be stably retained and grafted in a uniform distribution state in the culture, preferable proliferation ability and viability can be secured, further fixation treatment such as suture can be carried out in the transplantation into patients after the culture, and the mechanical strength is provided sustainable for (weighted) compression at the initial stage of transplantation.

As approaches thereof, use of various biodegradable plastics has been suggested. Vacanti et al. reported the production of a cultured cartilage using a scaffold obtained by converting a copolymer of glycolic acid and lactic acid (PLGA) to be porous by a salt elution method (U.S. Pat. No. 5,041,138). Moreover, the fore-mentioned Naughton et al. reported the production of a cultured cartilage comprising seeding cartilage cells and culturing them in a scaffold converted to be felt-like by polyglycolic acid, which is one of biodegradable plastics (International Publication WO 97/30662). However, although a certain level of performance can be secured in strength, particularly with the porous scaffold obtained by a salt elution method, there is a problem in grafting ability of cells. And the actual situation is that the cartilage production with a tissue formation in which cells are uniformly distributed similar to living bodies being secured is still in failure. Moreover, the scaffold converted to be felt-like by polyglycolic acid still has problems in grafting ability of cells, thus the situation is similar in failing to form uniform tissues.

As one of solution methods of these, Chen et al. reported the example of cartilage production using a scaffold comprising biodegradable plastic PLGA having the mechanical strength and collagen having cell grafting ability in combination (Chen et al., J. Biomed. Mater. Res., 2000, 51 volumes, 273-279 pages). However, in the actual situation that the safety of collagen itself is in question for such as mad cow disease, the development of the scaffold which does not use collagen as much as possible is desired.

As mentioned above, the porous scaffold using a biodegradable plastic conventionally developed has a problem in grafting ability of cells, and the present condition is that the cartilage production with a tissue formation in which cells are uniformly distributed similar to living bodies being secured is still in failure. Furthermore, for solving such problem, the example of cartilage production using a scaffold comprising collagen has been reported, but there is also a problem in view of the safety of collagen.

In addition, the defective part in cartilage has been pointed out to have problems of invasion of inflammatory cells from the subchondral bone, and formation of fibrous cartilage thereby, thus the cultured cartilage to be developed desirably have performance for preventing invasion of inflammatory cells in the transplantation. For this, as for the 3-dimensional porous scaffold to be used, the contact surface with the subchondral bone desirably has a structure for preventing invasion of inflammatory cells without inhibiting passage of a medium, etc.

Furthermore, the 3-dimensional porous scaffold desirably has characteristics that cells can be efficiently introduced at the stage of cell seeding, and the cells are hard to be leaked after the introduction.

SUMMARY OF THE INVENTION

The present inventors have made investigations for solving the above-mentioned problems, and as a result, they succeeded in development of a production of the scaffold which can solve these problems by a production method comprising rapid freeze-drying capable of temperature lowering at 3° C./minute as a key technology, and the production technology thereof.

That is, the first aspect of the invention relates to a 3-dimensional porous scaffold for tissue regeneration which comprises a structure composed of vertically long-shaped pores having a pore diameter of not less than 10 μm to not more than 500 μm and pore length of not less than 20 μm to not more than 1 cm being juxtaposedly arranged, and the spaces between the juxtaposed pores being communicated with small pores having a pore diameter of not more than 10 μm.

Further, the second aspect of the invention relates to
a process for producing the above 3-dimensional porous scaffold
which comprises
a) dissolving a scaffold material in an organic solvent,
b) pouring the prepared solution into a mold, and freezing the solution at a cooling rate of not slower than 3° C./minute, and
c) drying the frozen solution in vacuum to remove the organic solvent.

Further, the third aspect of the invention relates to
a 3-dimensional cell combination
which is obtainable by culturing a cell or precursor cell derived from a tissue in the above 3-dimensional porous scaffold in an artificial environment and/or the living body.

Further, the fourth aspect of the invention relates to
a process for producing a 3-dimensional cell combination
which comprises seeding a cell or precursor cell derived from a tissue in the above 3-dimensional porous scaffold, and culturing them in an artificial environment and/or the living body.

The scaffold of the present invention is excellent in retention and grafting abilities of cells, and by culturing a cell or precursor cell derived from a tissue in an artificial environment and/or the living body using this scaffold, it becomes possible to produce a 3-dimensional cell combination which can prevent invasion of inflammatory cells in the living organ transplantation and has similar characteristics with living body tissues in nature of having compatibility with surrounding tissues.

DETAILED DESCRIPTION OF THE INVENTION

The 3-dimensional porous scaffold for tissue regeneration of the present invention comprises a structure composed of vertically long-shaped pores having a pore diameter of not less than 10 μm to not more than 500 μm and pore length of not less than 20 μm to not more than 1 cm being juxtaposedly arranged, and the spaces between the juxtaposed pores being communicated with small pores having a pore diameter of not more than 10 μm.

The porous scaffold of the present invention has a structure composed of vertically long-shaped pores such as spindle shape, for instance, being juxtaposedly arranged. The pore diameter of said pores is not less than 10 μm to not more than 500 μm, and preferably not less than 20 μm to not more than 150 μm in view of securing a structure in which cells can be introduced and are hardly leaked. The pore length of said pores is not less than 20 μm to not more than 1 cm, but preferably not less than 50 μm to not more than 5 mm in view of retaining diffusivity of medium in the scaffold.

In the scaffold of the present invention, the spaces between the juxtaposed pores have a structure being communicated with small pores having a pore diameter of not more than 10 μm. The "structure being communicated with small pores having a pore diameter of not more than 10 μm" refers to a structure in which 50% or more, preferably 70% or more of the total number of said vertically long-shaped pores are connected with small pores having a pore diameter of not more than 10 μm each other. Through these small pores, a solution in a medium, etc. can passes, but cells cannot pass.

In the scaffold of the present invention, the porosity is preferably not less than 70%, but more preferably 70 to 95% in view of securing the cell density. Herein, the "porosity" refers to the total ratio of the vertically long-shaped pores and small pores in the scaffold, and is calculated from the weight of the scaffold material per unit volume.

Moreover, the pore diameter and pore length were calculated by measuring at least three scopes of inner diameters and length of pores present per unit scope by electron microscope observation and integrating the obtained data.

In the present invention, the term "for tissue regeneration" means to be for regeneration of various tissues constituting the living body.

As the structure of the porous scaffold of the invention, there may be mentioned a nonwoven fabric, foam, sponge, textile structure, etc., but preferred are foam or sponge structure in consideration of mechanical strength.

The shape of the porous scaffold of the invention is not particularly restricted provided that it is a 3-dimensional one, and for example, ones of flat plate-shape, sphere-shape such as a ball, and the like can be used. But flat plate-shape ones are preferred in view of securing medium diffusivity in the scaffold sufficiently and uniformly, and the like. Moreover, it is also possible to use ones obtained by producing a scaffold firstly in a flat plate-shape, and deforming thereof to a cylinder-shape having thickness (tube-shape) and the like shapes.

In the following, the porous scaffold of the invention is explained as taking a flat plate-shape one as an example.

This scaffold has pores of about 10 μm on both sides, and has the structure securing sufficient medium passage but in which cells hardly pass through. This structure is efficient for preventing the leakage of cells introduced into the scaffold as well as invasion of inflammatory cells from outside, particularly from the subchondral bone. In addition, as for the communicability between pores in the lateral direction, pores of not more than 10 μm in diameter are present for the communication through which a medium can pass, but cells cannot pass. Thus, the scaffold has the structure capable of giving a preferable condition for the growth of cells and preventing the leakage of seeded cells from the lateral sides.

As a more preferable aspect of the present invention, there may be mentioned
a 3-dimensional porous scaffold
which has an approximately flat plate-shape with vertically long-shaped pores in the thickness direction being juxtaposedly arranged in the surface direction, and one side face being subjected to pore-opening treatment.

Herein, the "thickness direction" refers to the vertical direction of the vertically long-shaped pores, and that "vertically long-shaped pores being juxtaposedly arranged in the surface direction" refers to that the vertically long-shaped pores are arranged in the same direction.

The "approximately flat plate-shape" includes a complete flat plate-shape of course, and also all of those similar to a flat plate-shape.

The "pore-opening treatment" refers to a treatment for enlarging a pore diameter, and for example, there may be mentioned a pore-opening treatment by a salt elution method, and a pore-opening treatment by a separation method, and the like as mentioned in below.

A salt elution method comprises a salt elution treatment operation called a leaching method only to the surface part of one side face in producing a scaffold. Thereby, it becomes possible to enlarge pores in one side face, and further by taking a funnel shape, the cell introduction into pores can be efficiently carried out.

The separation method comprises vertically separating a scaffold in the central region, namely in the flat plate direction, using the fact that the scaffold produced by the freeze-drying method of the invention mentioned below forms spaces or crystalline borders juxtaposedly with a wide surface in the central region of the thickness direction of vertically long-shaped pores such as a spindle shape. Thereby, on one surface (separated face), pores having 50 to 150 μm diameters on average can be secured in which cells can easily pass through.

The material of the porous scaffold of the invention is not particularly restricted, but preferably ones absorbed in the body under the physiological conditions, namely biocompatible materials. These include natural and synthetic ones.

As the biocompatible material constituting the porous scaffold, there may be mentioned one obtained from a natural product and one obtained by synthesis. But in view of workability, sterilization property and infection property, synthetic polymers decomposable by hydrolysis are preferred, and particularly preferred are hydrolysable polymers of α and β-hydroxycarboxylic acids. As examples of such biocompatible materials, there may be mentioned polylactic acid, polyglycolic acid, lactic acid/glycolic acid copolymer, poly ε caprolactone, lactic acid/ε caprolactone copolymer, etc.

As the copolymer to be used in the invention such as a copolymer of glycolic acid and lactic acid (PLGA), preferred are copolymers having the weight ratio between glycolic acid and lactic acid of 99:1 to 1:99, and particularly 75:25 to 25:75. Moreover, as for the other copolymer, the weight ratio of a comonomer other than lactic acid and lactic acid is preferably within the range of the weight ratio between glycolic acid and lactic acid mentioned above.

The scaffold of the invention can be adjusted to have appropriate thickness and necessary size for covering the affected part. The thickness of the scaffold of the invention is preferably 50 μm to 1 cm. In addition, for using the scaffold for treating knee or hip joint of human, one having the thickness of 1 to 3 mm is actually preferred.

Moreover, the shape and surface area of the above scaffold is not particularly restricted, and one having a sufficient size for covering the affected part can be produced. For example, when using for treating knee or hip joint of human, preferably, there may be mentioned one in cylindrical shape with 10 to 20 mm in diameter.

Next, the process for producing a 3-dimensional porous scaffold is explained.

The process for producing the 3-dimensional porous scaffold of the invention comprises the following steps:
  a) dissolving a scaffold material in an organic solvent,
  b) pouring the prepared solution into a mold, and freezing the solution at a cooling rate of not slower than 3° C./minute, and
  c) drying the frozen solution in vacuum to remove the organic solvent.

Meanwhile, said production process is also referred to as a freeze-drying method of the invention, and particularly, comprises the rapidly cooling at a cooling rate of not slower than 3° C./minute from both sides at the same time.

When dissolving these scaffold materials to make a solution thereof prior to the freeze-drying treatment, as a solvent, generally, various organic solvents can be used. Preferred are chloroform, dioxane, polyethylene glycol, etc.

Moreover, as for the mold into which the dissolved scaffold material is poured, the material thereof is not particularly restricted, but preferred are metal, glass, etc. sustainable for the freeze-drying treatment.

Furthermore, the form of said mold is not particularly restricted, and for example, an approximately flat plate-shape resemble to the structure of the cartilage is used in the case of treating cartilage damage. As long as it is based on the construction of the form of tissues aiming at regeneration, all of those efficient for treating affections can be used.

The solidification by freezing requires temperature lowering of at least 3° C./minute, that is to say rapid freezing of not slower than 3° C./minute is required. Said cooling rate is preferably not slower than 5° C./minute, and not faster than 10° C./minute. Moreover, it is preferable to rapidly cool from the both sides.

Said cooling rate is calculated from the time required for one prepared by pouring the solution obtained by dissolving the scaffold material in an organic solvent into a mold being placed in a freezer at −40° C. solidifies.

The above cooling rate (temperature lowering) becomes possible by using, for example, an ultradeep freezer or liquid nitrogen. Particularly, it is preferable to rapidly cool from the both sides of the scaffold material-containing solution (prepared by pouring said solution into a mold and covering with a glass plate, etc. on the top surface) by contacting blocks (objects) cooled to −40° C.

Thereafter, the frozen solution is dried in vacuum to remove an organic solvent, thereby a 3-dimensional porous scaffold can be obtained.

The 3-dimensional porous scaffold which has an approximately flat plate-shape with vertically long-shaped pores in the thickness direction being juxtaposedly arranged in the surface direction, and one side face being subjected to pore-opening treatment, which is one preferable aspect of the present invention, can be produced by the following steps using the separation method:
  a) dissolving a scaffold material in an organic solvent,
  b) pouring the prepared solution into a mold forming an approximately flat plate-shape, and freezing the solution at a cooling rate of not slower than 3° C./minute,
  c) drying the frozen solution in vacuum to remove the organic solvent, and
  d) separating the dried scaffold in the central region of the thickness direction in the flat plate direction.

In this specification, "separating in the central region of the thickness direction in the flat plate direction" refers to vertically separate a flat plate near the central part of the thickness direction of a scaffold.

The 3-dimensional porous scaffold which has an approximately flat plate-shape and one side face being subjected to pore-opening treatment can also be produced by the following steps using a salt elution method:
  a) dissolving a scaffold material in an organic solvent,
  b) dispersing a granular salt in a mold forming an approximately flat plate-shape,
  c) pouring the prepared solution into said mold, and freezing the solution at a cooling rate of not slower than 3° C./minute,
  d) drying the frozen solution in vacuum to remove the organic solvent, and
  e) removing the granular salt by washing with water.

Herein, the granular salt refers to a crystalline substance having a particle diameter of not more than 5000 μm, and there may be mentioned inorganic salts such as KCl, NaCl and $CaCl_2$, various ammonium salts, salts of organic compounds such as trisodium citrate, and the like. In view of the particle diameter, trisodium citrate is particularly preferred.

The particle diameter of the granular salt is preferably 50 to 2000 μm, and more preferably 200 to 800 μm.

When a 3-dimensional porous scaffold is produced by the method of the invention using a salt elution method, the obtained scaffold has the structure composed of pores produced by the salt elution treatment in 1 to 50% of the thickness of the scaffold, and the above vertically long-shaped pores in the remaining 50% to 99%.

The 3-dimensional cell combination of the invention is obtainable by culturing a cell or precursor cell derived from a tissue in the 3-dimensional porous scaffold of the invention in an artificial environment and/or the living body.

The 3-dimensional cell combination as mentioned in the present invention refers to an analog of organs and tissues of the living body produced by seeding a cell or precursor cell derived from a tissue in the scaffold of the invention and culturing them in an artificial environment and/or the living body.

As the cell or precursor cell derived from a tissue to be used in the practice of the invention, usable are, for example, cells or precursor cells derived from organs and tissues of the living body such as a bone, cartilage, ligament, tendon, blood vessel, skin, fat, muscle, nerve, heart, liver, pancrea, intestine, kidney, cornea, bladder, ureter, urethra, breast; and stem cells such as mesenchymal stem cell derived from marrow or cord blood.

Among these, in view of simplicity of the tissue structure, ones derived from a bone, joint cartilage, ligament and tendon are preferred. Moreover, in view of easiness of sampling and having high differentiation ability to various differentiation, ones derived from marrow, fat, liver and cord blood are preferably used, and mesenchymal stem cell one is more preferably used.

Furthermore, said 3-dimensional cell combination preferably has characteristics close to those of the organs and tissues of the living body, because said combination is used for tissue regeneration. The "characteristics close to the tissues" means that the degree of tissue formation obtained from the number of cells calculated by tissue staining is not less than 70% of the living body.

As the pigment to be used for the tissue staining, there may be mentioned, for example, Alcian blue, Hematoxylin, Hematoxylin-eosin, Alizarine red, Safranine O, Toluidine blue, etc.

In this specification, "culturing in an artificial environment" means to carry out the culture outside the living body in such as a test tube and incubator.

In addition, "culturing in the living body" means to carry out the culture in the living tissue, for example, a culture of cells by placing a scaffold in the living tissue.

As the 3-dimensional cell combination of the invention, there may also be mentioned a 3-dimensional cell combination having not less than $1/10$ compression modulus of the normal cartilage which is obtained by culturing a cartilage cell or precursor cell derived from a tissue in the 3-dimensional porous scaffold produced by the method of the invention using a salt elution method, the obtained scaffold in an artificial environment and/or the living body.

According to the mechanical strength measurement conditions as used in the practice of the invention, the compression modulus of said 3-dimensional cell combination is within the strength range of from the average level of the normal cartilage to about not less than $1/10$ of the normal cartilage, more specifically $1.5 \times 10^{-1}$ MPa to 2.0 Mpa. That the combination has the strength in the average level or lower of the normal cartilage can be said as quite a efficient characteristic to prevent damaging the opposite side of cartilage tissue when said 3-dimensional cell combination is actually embedded in an affected part. In addition, said compression modulus is obtained in the part except for the part subjected to pore-opening treatment (internal structure) in the 3-dimensional cell combination.

Herein, the mechanical strength measurement condition in the practice of the invention comprises equilibrating the produced 3-dimensional cell combination in a PBS (phosphate buffered saline) solution at 25° C. for 30 minutes, and compressing at a head speed of 0.1 mm/second.

The compression modulus represents a rate of change to distortion of the stress given at the time of compression. The compression modulus can be determined with a control analysis software attached on "Texture analyzer TA-XT2i (product of Stable Micro Systems Ltd.)" according to ASTM: D 1621-94.

As another 3-dimensional cell combination according to the invention, there may also be mentioned
a 3-dimensional cell combination
which is obtainable by culturing a cartilage cell or precursor cell derived from a tissue in the 3-dimensional porous scaffold produced by the process according to the invention using a salt elution method in an artificial environment and/or the living body, and
has a tissue structure more similar to the normal cartilage with the thickness from the side subjected to pore-opening treatment or side not subjected to pore-opening treatment being within the range of 1 to 90% of the whole thickness.

Herein, "the whole thickness" refers to length in the width direction from the side not subjected to pore-opening treatment to the side subjected to pore-opening treatment. Further, "a tissue structure more similar to the normal cartilage" refers to a structure having the degree of tissue formation obtained from the number of cells calculated from tissue staining is not less than 70%, and mechanical strength of not less than $1/10$ of the normal cartilage.

Next, the process for producing the 3-dimensional cell combination of the invention is explained.

The above production process comprises seeding a cell or precursor cell derived from a tissue in the 3-dimensional porous scaffold of the invention in an artificial environment and/or the living body.

In the above production process, the cell or precursor cell derived from a tissue can be seeded by the well-known method, but it is preferable to sow the cell or precursor cell at a density of $10^6$ to $10^8$ cells per 1 cm$^3$ of the scaffold.

In the above method, the cell or precursor cell derived from a tissue is preferably subjected to a stand culture under 3-dimensional environment for 1 to 48 hours beforehand in view of fixation of the cell to the scaffold.

Herein, "culturing under 3-dimensional environment" means to carry out the culture in the state that a lump of cells is formed. Such culture is called micromass culture. As a specific method of this culture, there may be mentioned, for example, a method comprising putting $10^5$ to $10^7$ cells per well in a 96-well flat plate and culturing, and the like.

In seeding and culturing the cell or precursor cell derived from a tissue in the scaffold of the invention, it is allowable that various additive factors are concomitantly present in order to promote the cell production. As the additive factor, there may be mentioned, for example, polymer protein factors such as bFGF (basic fibroblast growth factor), BMP (bone morphogenetic factor), TGF-β (transformation growth factor β), IGF (insulin-like growth factor), and PDGF (platelet-derived growth factor); mucopolysaccharides such as hyaluronic acid and chondroitin; and various vitamins such as ascorbic acid, tocopherol and coenzyme Q10, and the like.

Since the culture in the presence of ascorbic acid is quite effective in cell proliferation and tissue production, ascorbic acid is particularly preferred as the above additive factor.

The level of addition of the above additive factor depends on the species of said factor, but the additive factor is preferably added in such amount that the final concentration in a medium becomes 0.001 to 1000 μg/ml.

Moreover, in the process for producing the 3-dimensional cell combination of the present invention, the culture in an artificial environment is preferably carried out under the conditions that a culture fluid is moved at a rate of 0.1 cm per second to 50 cm per second relative to the scaffold in view of supplying a flesh medium to the 3-dimensional cell combination or removing waste matters from the 3-dimensional cell combination.

Furthermore, in the production of the cartilage in Examples of the invention mentioned below, cells sampled from the joint are proliferated by flat plate culture, subjected to micromass culture, and then seeded on a scaffold. Such process was carried out for recovering cartilage functions which has been lowered because of the flat plate culture, and in fact, expressions of proteoglycan, a functional marker of a cartilage cell, and mRNA of II-type collagen, and recovering of protein itself were confirmed.

In the 3-dimensional cell combination produced by the above-mentioned method, for example, taking the cartilage tissue produced in Examples of the invention mentioned below as an example, as a result of tissue staining evaluation using Alcian blue pigment, portions strongly stained with Alcian blue were eccentrically located on the side not subjected to pore-opening treatment, and normal type of cartilage formation proceeded on this side. On the contrary, on the side subjected to pore-opening treatment, portions weakly stained with Alcian blue were eccentrically located, and it was showed that portions in which tissue formation did not proceed were eccentrically located on this side. Such deflection of tissue formation is considered to be advantageous structure in securing the consistency of a graft with surrounding tissues (bone, cartilage) in medical treatment using said cultured cartilage tissue.

Moreover, by transplanting the 3-dimensional porous scaffold or 3-dimensional cell combination of the present invention into the living body, cartilage damage can be particularly effectively treated.

BRIEF EXPLANATION OF THE DRAWINGS

FIG. 16B represents a view showing appearance photographs of an affected part and the results of tissue staining of an affected part after the lapse of 12 weeks of treatment of cartilage defect using a PLGA scaffold seeded with a mesenchymal stem cell in a rabbit as shown in Example 11 (Hematoxylin-eosin (HE) stain, Alcian blue (AB) stain).

BEST MODE FOR CARRYING OUT THE INVENTION

In the following, the present invention is described in detail by means of examples, but these are no limitative of the scope of the invention.

EXAMPLE 1

Process for Producing a PLGA Scaffold a. A Process for Producing a PLGA Scaffold Subjected to Pore-opening Treatment by a Salt Elution Method A lactic acid/glycolic acid copolymer (weight ratio=75:25), which is a biocompatible material, was dissolved in dioxane, and the concentration of said copolymer was adjusted to 4% by weight. In a mold produced with a glass-plate, trisodium citrate in which those having a diameter of about not more than 212 μm and about not less than 850 μm were removed using sieves having a diameter of 212 μm and a diameter of 850 μm was dispersed as a granular salt so as to be about 0.05 g/cm$^2$. The above prepared solution was poured therein so as to be 2 mm in thickness, and the mold was covered with a glass plate. Then, the mold was placed in a freezer at −40° C., and blocks (objects) cooled at −40° C. were brought into contact from both sides to rapidly freeze the mold (at a cooling rate of 5° C./minute). After the freezing, dioxane was removed by drying in vacuum at −0.1 MPa for 48 hours. After the drying, the content was separated from the mold and the granular salt was washed away with flowing water. By sufficiently drying the resultant, a scaffold was obtained.

Figure 1:
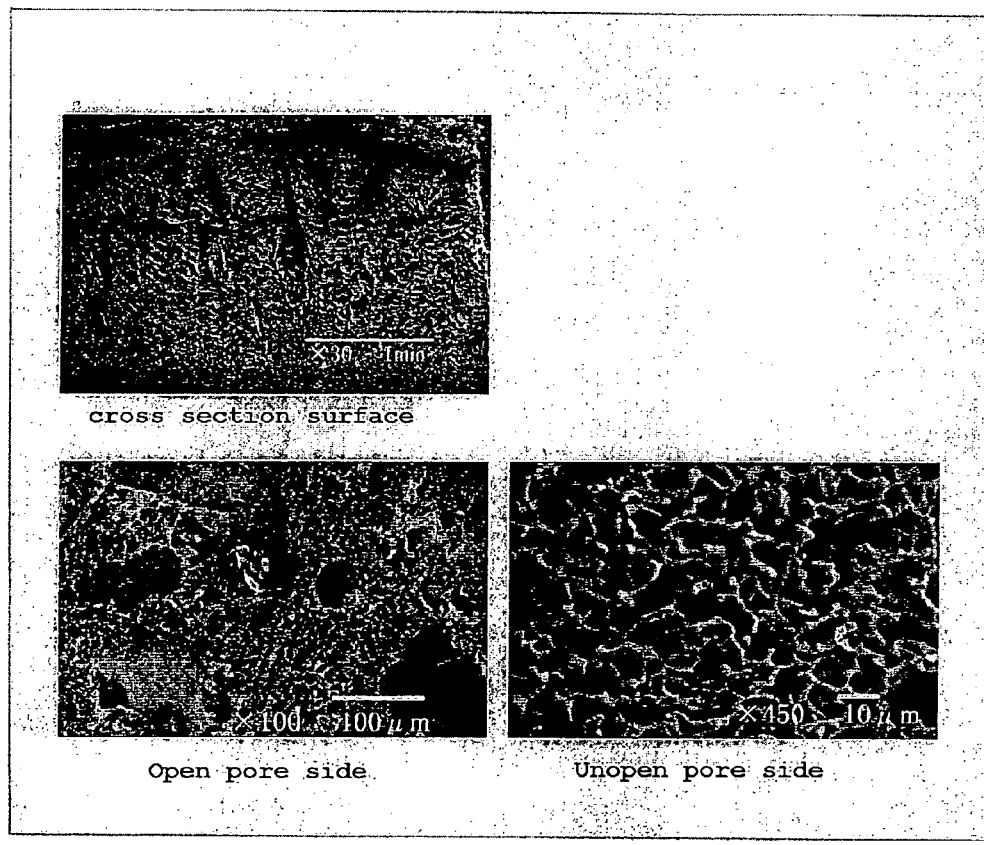
FIG. 1 represents electron micrographs showing a section of the scaffold of the invention viewed from the thickness direction, a surface viewed from the side subjected to pore-opening treatment, and a surface viewed from the side not subjected to pore-opening treatment.

In FIG. 1, electron micrographs showing a section viewed from the thickness direction, a surface viewed from the side subjected to salt elution treatment (i.e. a surface viewed from the side subjected to pore-opening treatment), and a surface viewed from the side not subjected to pore-opening treatment of the obtained scaffold were shown. Pores of the side subjected to pore-opening treatment were confirmed to be larger compared with those of the side not subjected to pore-opening treatment. In addition, the thickness of the salt elution-treated part of the scaffold produced by a salt elution method was 15% of the entire scaffold.

b. A Process for Producing a PLGA Scaffold Subjected to Pore-opening Treatment by a Separation Method A lactic acid/glycolic acid copolymer (weight ratio=75:25), which is a biocompatible material, was dissolved in dioxane, and the concentration of said copolymer was adjusted to 4% by weight. In a mold produced with a glass-plate, the above prepared solution was poured so as to be 2 mm in thickness, and the mold was covered with a glass plate. Then, the mold was placed in a freezer at −40° C., and blocks (objects) cooled at −40° C. were brought into contact from both sides to rapidly freeze the mold (at a cooling rate of 5° C./minute). After the freezing, dioxane was removed by drying in vacuum at −0.1 MPa for 48 hours. After the drying, the content was separated from the mold and sufficiently dried. Then, it was separated in the central region of the thickness direction in the flat plate direction, a scaffold was obtained.

COMPARATIVE EXAMPLE 1

Structure of a Scaffold Produced by the Conventional Freeze-drying Method

As a comparison control of the present invention, a PLGA scaffold was produced by the usual (conventional) freeze-drying method. That is, a lactic acid/glycolic acid copolymer (weight ratio=75:25) was dissolved in dioxane, and the concentration of said copolymer was adjusted to 4% by weight. In a glass mold, the above solution was poured so as to be 2 mm in thickness. By freezing the mold only from one side, drying in vacuum, removing dioxane and then drying, a PLGA scaffold was produced.

Figure 2A:
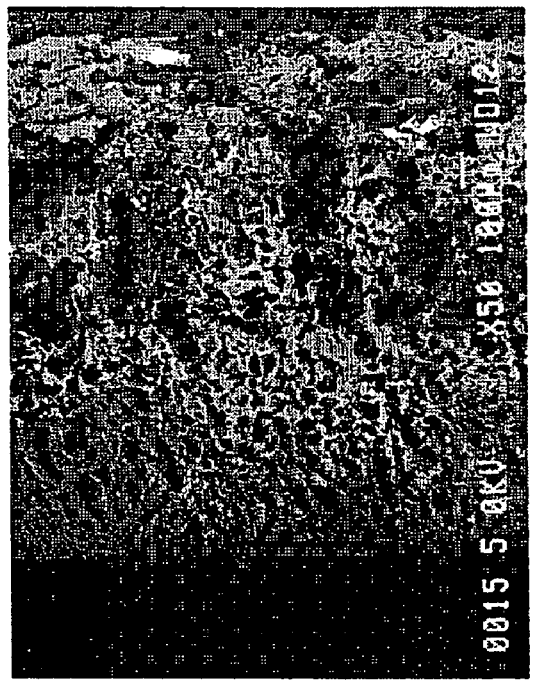
FIG. 2A is an electron micrograph showing a section of the scaffold produced by the freeze-drying method according to the invention viewed from the thickness direction.
Figure 2B:
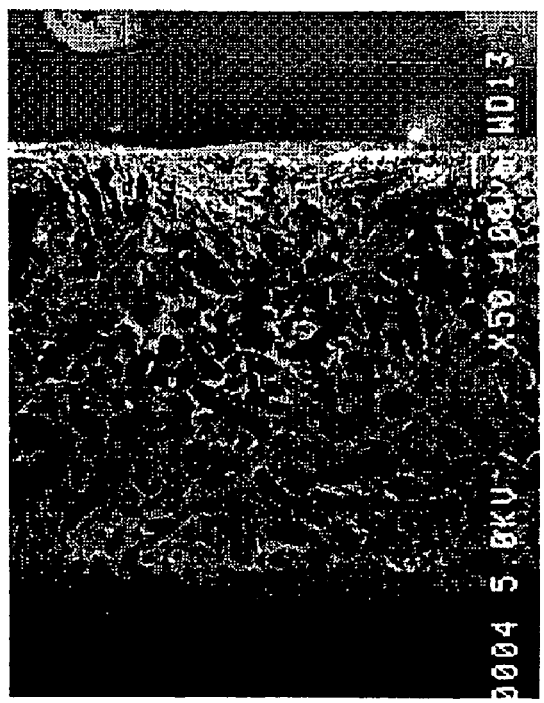
FIG. 2B is an electron micrograph showing a section of the scaffold produced by the conventional freeze-drying method viewed from the thickness direction.

In FIG. 2A, an electron micrograph analysis image of the section of the scaffold produced by the method of the invention (Example 1-a) was shown, and in FIG. 2B, an electron micrograph analysis image of the section of the scaffold produced by the conventional freeze-drying method (Comparative Example 1) was shown. The scaffold produced by the method of the invention had a structure composed of vertically long-shaped pores being juxtaposedly arranged, and the spaces between the juxtaposed pores being communicated with small pores having a pore diameter of not more than 10 μm. On the contrary, the scaffold produced by the conventional method was poor in continuity and directivity of pores, and a pore having an enough size equivalent to that produced by the pore-opening treatment of the invention was not found. Moreover, it had thickness unevenness, and it was found that these scaffolds had obviously different pore shapes and structures.

Furthermore, an experiment using the PLGA scaffold produced by the separation method of Example 1-b was carried out in the same manner, and the equivalent result was confirmed as one obtained by a salt elution method of Example 1-a.

EXAMPLE 2

Production of a Cultured Cartilage Using a PLGA Scaffold

A cartilage tissue was sampled from the knee joint of a Japanese Saanen goat of about 1 year old to separate a cartilage cell with collagenase. The cell was cultured using Ham's F-12 medium containing 10% bovine fetal serum and ascorbic acid with the final concentration of 50 μg/ml. The cartilage cells subjected to passage culture for 2 times were added to a 96-well tissue culture plate in $1 \times 10^6$ per well and subjected to micromass culture for overnight (about 16 hours) to be used for producing a cultured cartilage.

The PLGA scaffold produced by a salt elution method of Example 1-a and sterilized with γ-ray at 25 KGry was placed in the above medium, and deaerated under reduced pressure to spread the medium on the scaffold surface. Then, the cartilage cells subjected to micromass culture were seeded at the density of $1 \times 10^7$ per 1 cm³ of the scaffold. The scaffold seeded with the cartilage cells was placed in a culture petri dish, said medium was added thereon to the level that the scaffold was covered, and the resultant was subjected to stand culture overnight. Thereafter, the scaffold was moved to a 10 cm-diameter culture petri dish containing 20 ml of said medium, and rotational culture was carried out at the rotation rate of 30 rpm using a shaking machine capable of conducting horizontal circular motion. At the 14th day from the start of the rotational culture, the scaffold was taken out, and the produced cultured cartilage was evaluated histrogically and biochemically (ELISA: Enzyme-Linked-Immuno-Sorbent-Assay).

Figure 3:
FIG. 3 shows staining of a cultured cartilage tissue (Alcian blue staining).
Figure 4:
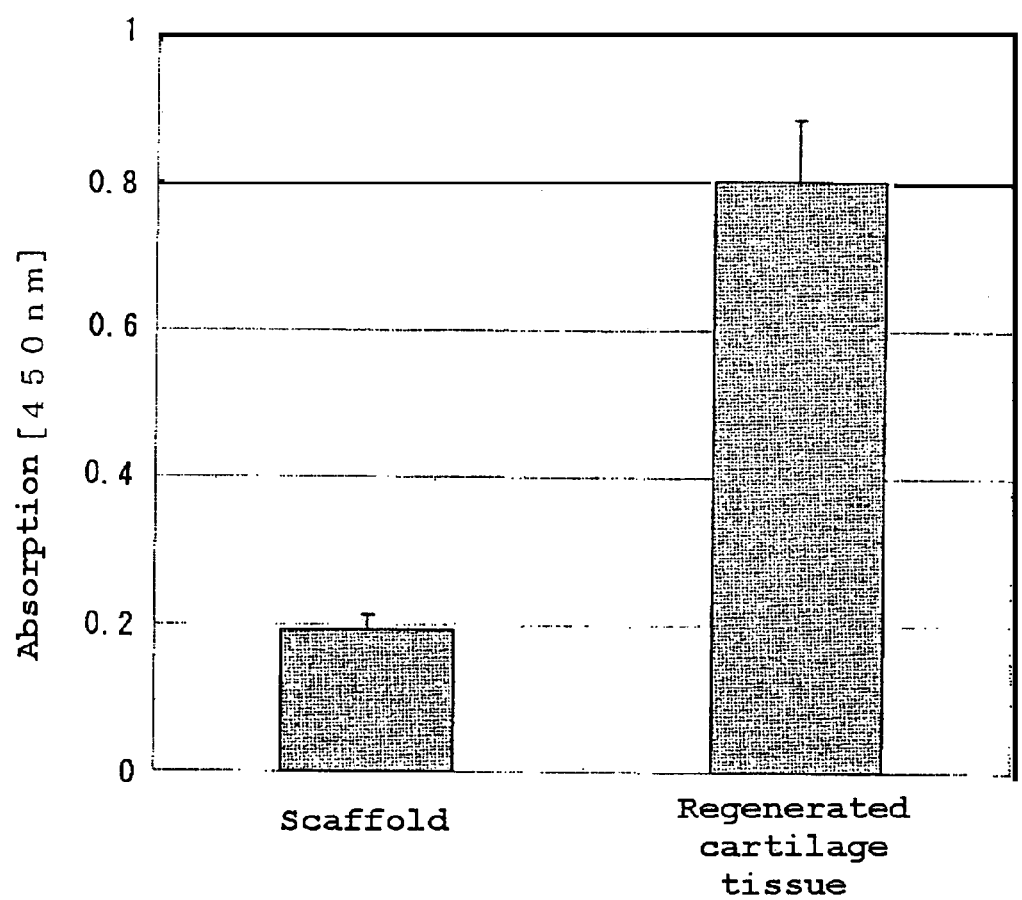
FIG. 4 shows the result of ELISA determination of a cultured cartilage proteoglycan (aggrecan).
Figure 5:
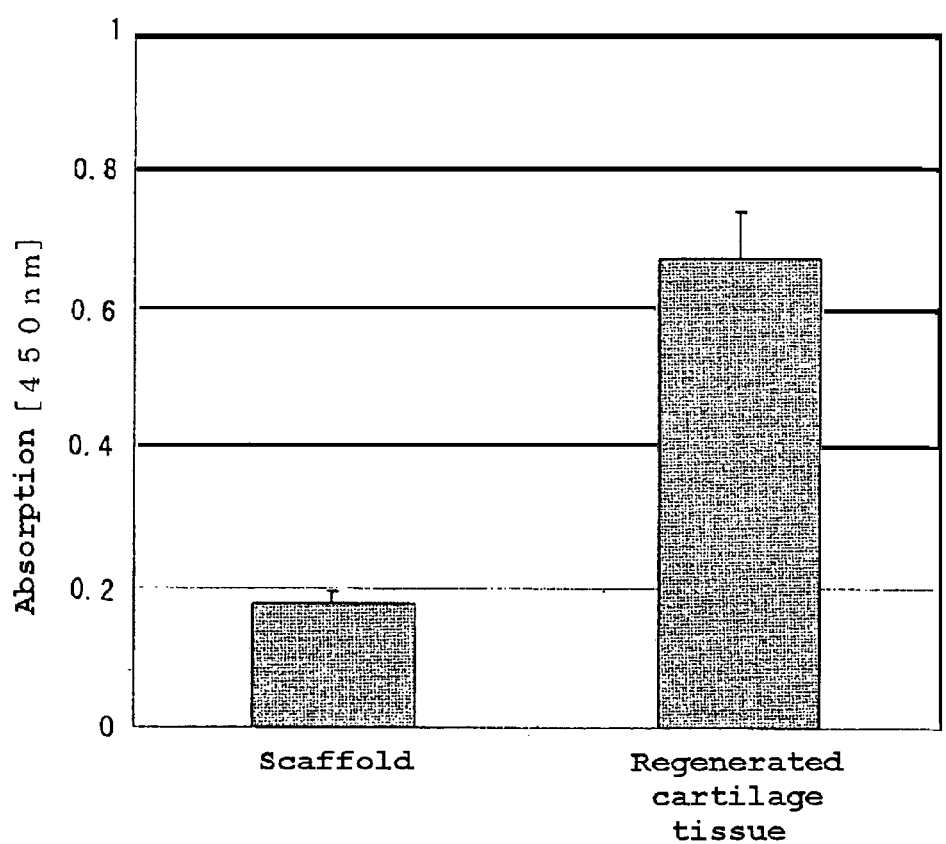
FIG. 5 shows the result of ELISA determination of a cultured cartilage II-type collagen.
Figure 6:
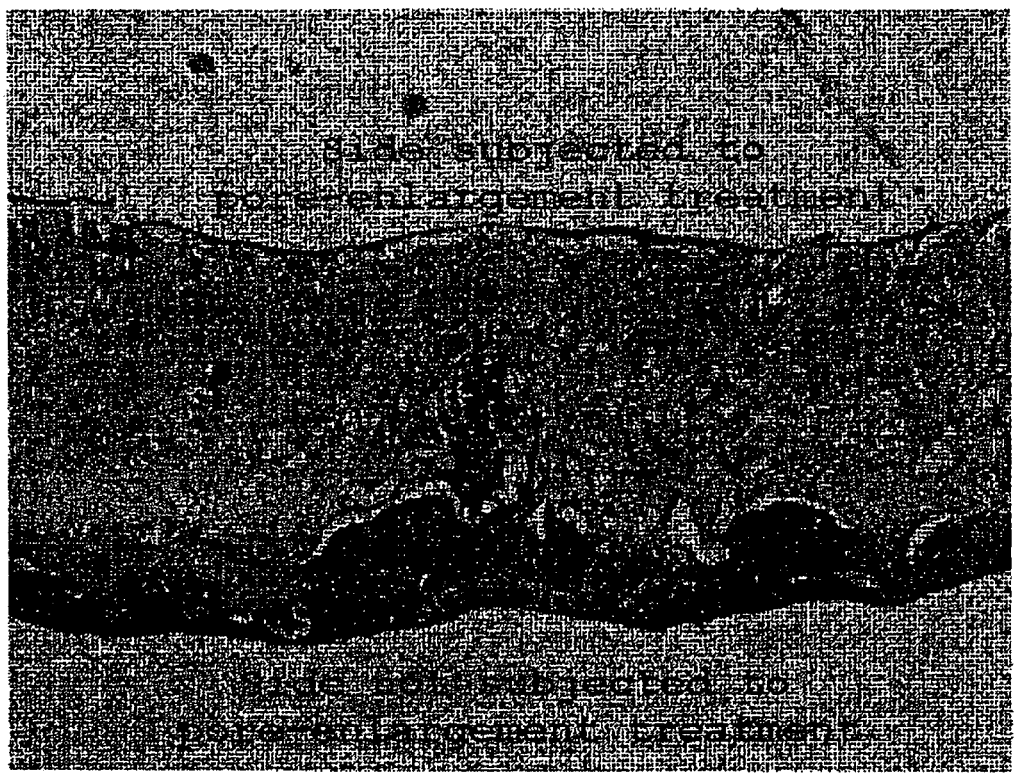
FIG. 6 shows the result of staining of a cultured cartilage tissue (Alcian blue staining).

The tissue image of the cultured cartilage produced using this PLGA scaffold exhibited remarkable Alcian blue positivity as shown in FIG. 3. Furthermore, the cartilage cells present in these tissues did not have fibroblast shape, but had very resemble shape with permanent cartilage cells (FIG. 3). This cultured cartilage was solubilized with 4 M guanidine hydrochloric acid solution, and the detection of agrecan, which is a characteristic proteoglycan of cartilage, and II-type collagen, which is a characteristic collagen of cartilage, were attempted by ELISA. Then, the presences of agrecan and II-type collagen were confirmed (FIG. 4 and FIG. 5). Moreover, this PLGA scaffold has the structural characteristic of having micropore structure in which pores in one side were enlarged and pores in the other side inhibit passage of cells. In the produced cultured cartilage, polarity of tissue formation was found that Alcian blue was most positive and the form of cells was quite similar with permanent cartilage cells in the side not subjected to pore-opening treatment (pores not being enlarged), and in the side subjected to pore-opening treatment (pores being enlarged), Alcian blue staining was remained slightly weak (FIG. 6).

Furthermore, an experiment using the PLGA scaffold produced by the separation method of Example 1-b was carried out in the same manner, and the equivalent result was confirmed as one obtained by a salt elution method of Example 1-a.

EXAMPLE 3

Comparison of Cell Retention Ability of the PLGA Scaffold Produced by the Method According to the Invention Cartilage cells were seeded on the PLGA scaffold (referred to as scaffold A) produced by a salt elution method of Example 1-a, and the cell retention ability was examined. The cartilage cells were prepared and seeded on the scaffold by the method described in Example 2. scaffold A was formed to a disc shape having 10 mm in diameter and 1 mm in thickness (volume 78.5 mm$^3$), and 30 µl of a cartilage cell suspension prepared to have a cell concentration of $5\times10^7$ cells/ml was seeded respectively thereon. The resultant was allowed to stand for 1 hour on a culture petri dish, and then the number of cells leaked from the scaffold was counted (Table 1).

As shown in Table 1, in scaffold A, the number of leaked cells detected in the medium was 0.033% of the seeded cells. This was significantly higher than the cell retention ability of the PLGA scaffold (scaffold B) produced by a conventional method (salt elution method) shown in Comparative Example 2 below.

Furthermore, an experiment using the PLGA scaffold produced by the separation method of Example 1-b was carried out in the same manner, and the equivalent result was confirmed as one obtained by a salt elution method of Example 1-a.

COMPARATIVE EXAMPLE 2

Cell Retention Ability of the PLGA Scaffold Produced by the Conventional Salt Elution Method Cartilage cells were seeded on the PLGA scaffold (referred to as scaffold B) produced by the conventional salt elution method, and the cell retention ability was examined. The PLGA scaffold was produced according to the method of Mikos et al. (Biomaterial, 1993, 14 volumes, 323-330 pages), which has pores being formed attributable to salt particles in the entire scaffold. The preparation of the cartilage cells, seeding on the scaffold, and count of the number of leaked cells were conducted according to the methods described in Examples 2 and 3. The results were shown in Table 1.

From these results, it is found that in the scaffold prepared by the conventional salt elution method, a considerable number of cells in the seeded cell suspension was leaked.

TABLE 1 comparison of cell retention ability

| | Scaffold A | Scaffold B |
|---|---|---|
| Volume of the seeded cell suspension | 30 µl | 30 µl |
| Number of the seeded cells (a) | $1.5 \times 10^6$ cells | $1.5 \times 10^6$ cells |
| Amount of the leaked medium | 10 µl | 10 µl |
| Number of cells in the leaked medium (b) | Up to 500 cells | up to $2.5 \times 10^5$ cells |
| Rate of the leaked cells (b/a × 100) | 0.033% | 16.7% |

COMPARATIVE EXAMPLE 3

Cell Retention Ability of the PLGA Scaffold Produced by the Conventional Freeze-drying Method In the same manner as in Comparative Example 2, the cell retention ability of the scaffold produced by the conventional freeze-drying method (Comparative Example 1) was examined.

As a result, whereas the scaffold according to the invention retained 99% of the seeded cells as shown in Example 3, the scaffold produced by the conventional freeze-drying method only retained not more than 1% of cells.

EXAMPLE 4

Degree of Tissue Formation of a Cultured Cartilage Produced Using the PLGA Scaffold Produced by the Method According to the Invention (Tissue Staining)

Cartilage cells were seeded on the PLGA scaffold (scaffold A) produced by a salt elution method of Example 1-a, and the degree of tissue formation was compared. The preparation of cartilage cells, seeding on the scaffold, and culture of the seeded cells were conducted according to the method described in Examples 2. In the 30th day from the start of the rotational culture, scaffold A was taken out and histologically evaluated. The Hematoxylin-eosin staining image and Alcian blue staining image of regenerated cartilage tissue segment were shown in FIG. 7.

Figure 7:
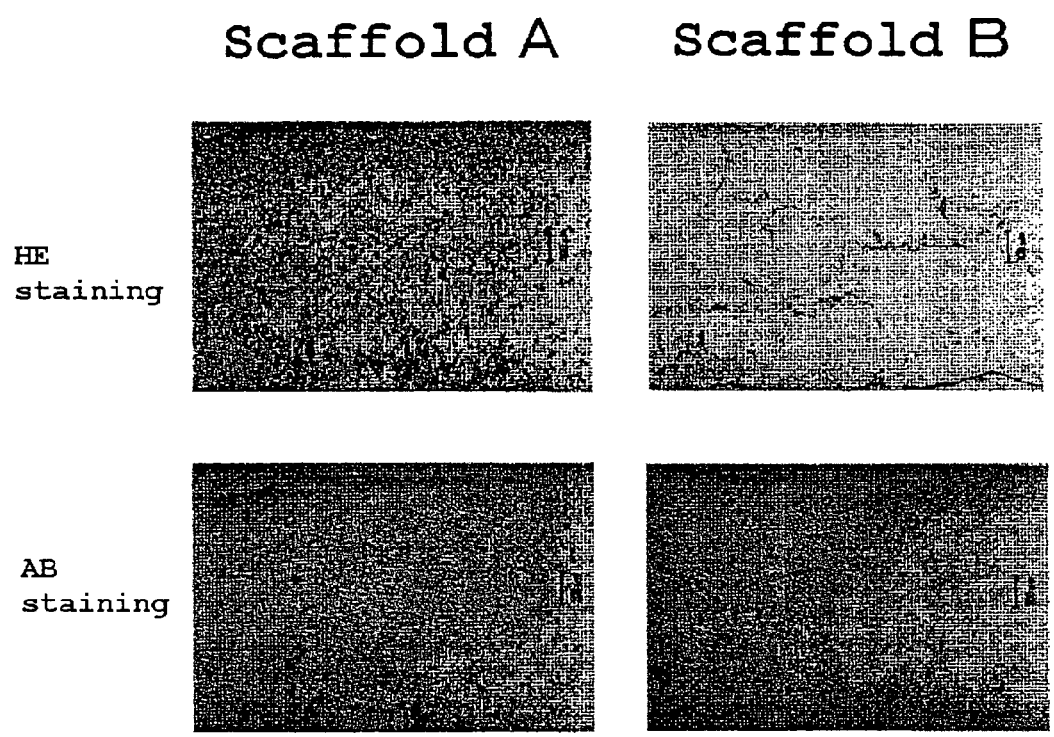
FIG. 7 shows cultured cartilage tissue staining views showing the comparison results of cultured cartilage tissue staining properties by Hematoxylin-eosin (HE) staining and Alcian blue (AB) staining in scaffold A of the present invention and scaffold B produced by the conventional salt elution method.

As shown in FIG. 7, the cultured cartilage produced using the PLGA scaffold of the invention has approximately equivalent cell density as the normal cartilage, and also Alcian blue staining exhibited positive result.

Furthermore, an experiment using the PLGA scaffold produced by the separation method of Example 1-b was carried out in the same manner, and the equivalent result was confirmed as one obtained by a salt elution method of Example 1-a.

COMPARATIVE EXAMPLE 4

Degree of Tissue Formation of a Cultured Cartilage Produced Using the PLGA Scaffold Produced by the Conventional Method (Salt Elution Method) (Tissue Staining)

Except that scaffold B of Comparative Example 2 was used, the same procedure was carried out as in Example 4. The result was shown in FIG. 7.

As shown in FIG. 7, the degree of tissue formation of a cultured cartilage produced using the PLGA scaffold produced by the conventional method (salt elution method) was exceedingly poor as compared with the degree of tissue formation of a cultured cartilage produced using the PLGA scaffold produced by the method according to the invention.

EXAMPLE 5

Effect of Ascorbic Acid on Generation of a Cultured Cartilage

By the procedure as shown in below, the effect of ascorbic acid on generation of a cultured cartilage was examined. By the method described in Example 2, a cartilage cell was prepared and seeded on the PLGA scaffold produced by a salt elution method of Example 1-a. This scaffold was cultured respectively in Ham's F-12 medium containing ascorbic acid with the final concentration of 50 µg/ml, and in a medium not containing ascorbic acid for 2 weeks, and the degree of formation of cartilage tissues was examined by Alcian blue staining.

Figure 8A:
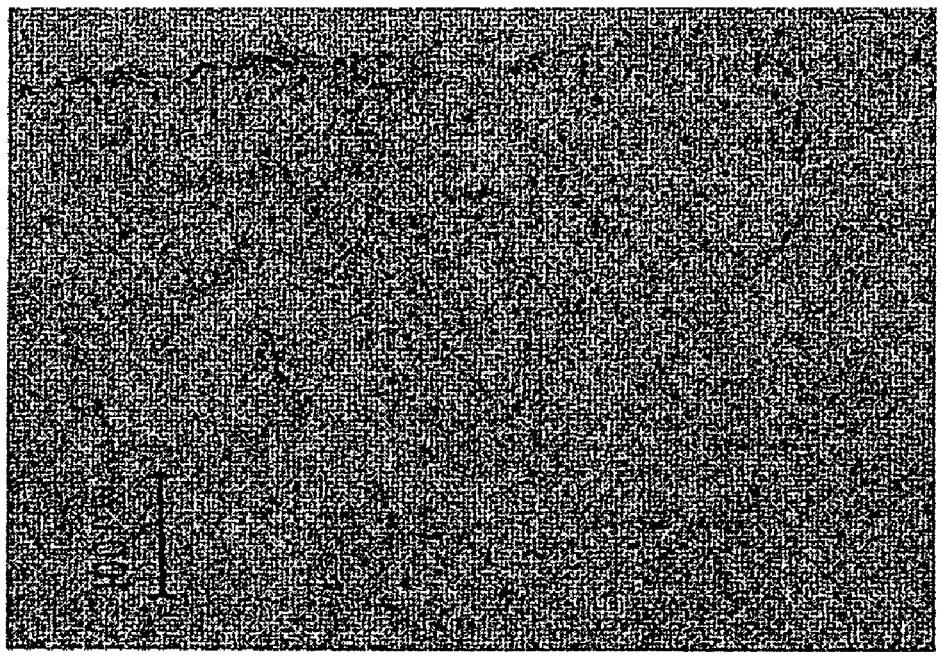
FIG. 8A shows the result of cultured cartilage tissue staining (Alcian blue staining) when the culture was carried out in a medium not containing ascorbic acid.
Figure 8B:
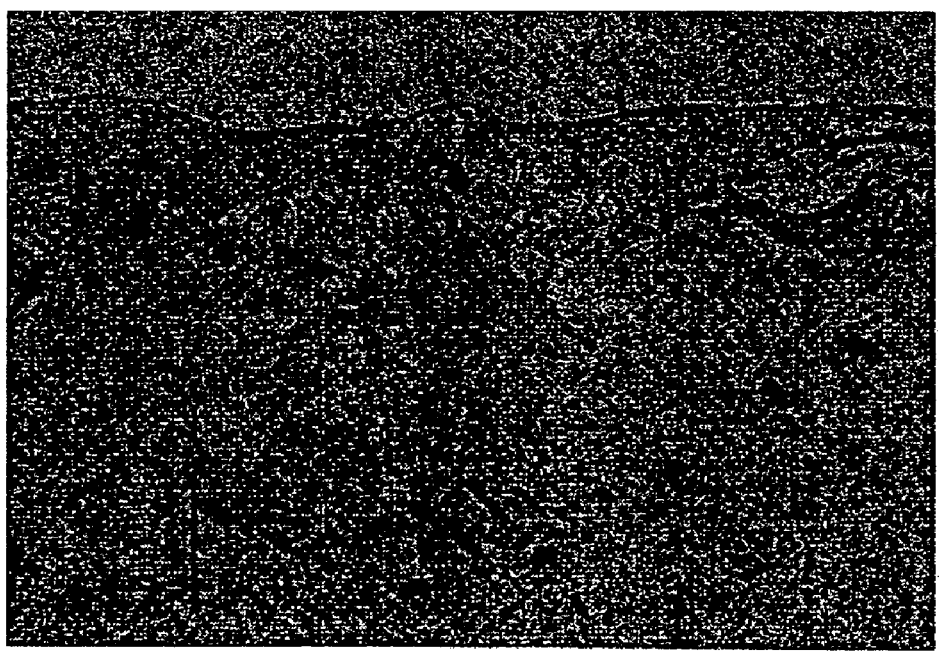
FIG. 8B shows the result of cultured cartilage tissue staining (Alcian blue staining) when the culture was carried out in a medium containing ascorbic acid (50 μg/ml).

As shown in FIG. 8A and FIG. 8B, the formation of cartilage tissues was remarkably improved by the addition of ascorbic acid to the medium.

Furthermore, an experiment using the PLGA scaffold produced by the separation method of Example 1-b was carried out in the same manner, and the equivalent result was confirmed as one obtained by a salt elution method of Example 1-a.

EXAMPLE 6

Effect of Micromass Culture on the Formation of a Cultured Cartilage

By the procedure as shown in below, the effect of micromass culture on the formation of a cultured cartilage was examined. By the method described in Example 2, a cartilage cell was prepared, added with $1\times10^6$ cells per well of a 96-well culture plate, and allowed to stand for 16 hours in a $CO_2$ incubator to carry out micromass culture. These cells were seeded on the scaffold produced in Example 1 by the method described in Example 2, and rotational culture was carried out for two weeks. Alcian blue staining of the cultured cartilage thus produced by micromass culture and the tissue produced by without carrying out micromass culture were compared (FIG. 9A and FIG. 9B).

Figure 9A:
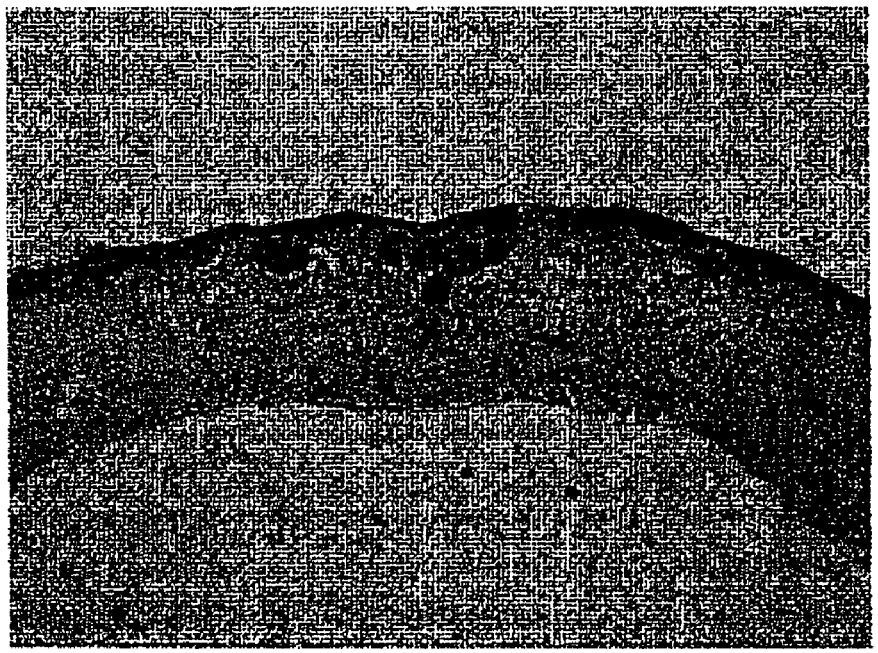
FIG. 9A shows the result of cultured cartilage tissue staining (Alcian blue staining) when micromass culture was carried out.
Figure 9B:
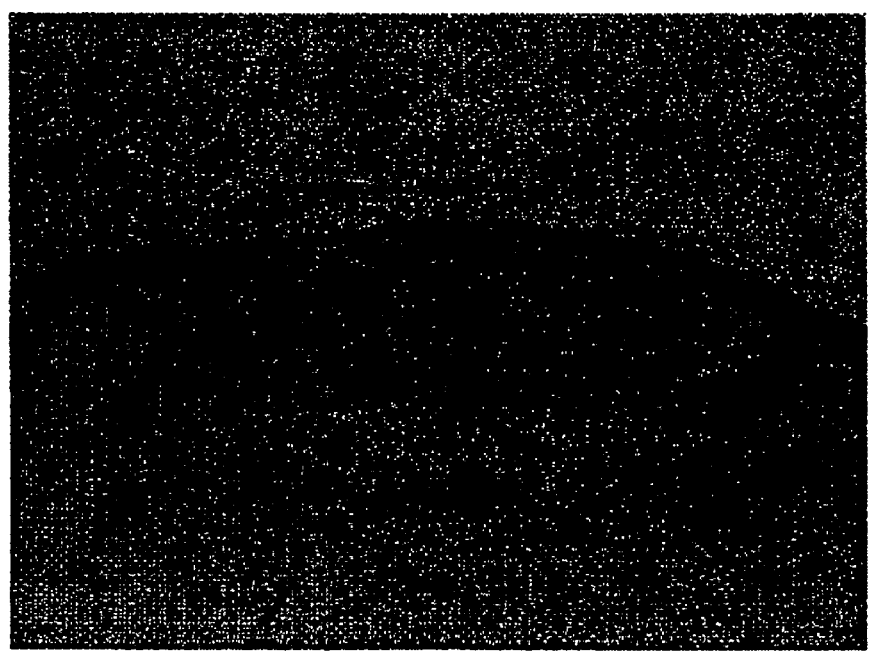
FIG. 9B shows the result of cultured cartilage tissue staining (Alcian blue staining) when micromass culture was not carried out.

As shown in FIG. 9A and FIG. 9B, Alcian blue staining in the cultured cartilage produced by micromass culture was preferable as compared with that produced by without carrying out micromass culture.

EXAMPLE 7

Measurement of Mechanical Strength of a Cultured Cartilage

A cultured cartilage was produced by the method described in Example 2 using the PLGA scaffold produced by a salt elution method of Example 1-a, and made into a cultured cartilage module of 6.5 mm in diameter and 1.5 mm in thickness. This module was equilibrated in a PBS solution at 25° C. for 30 minutes, and the stress received when the compression was applied at a head speed of 0.1 mm/second was measured by the following method.

Figure 10:
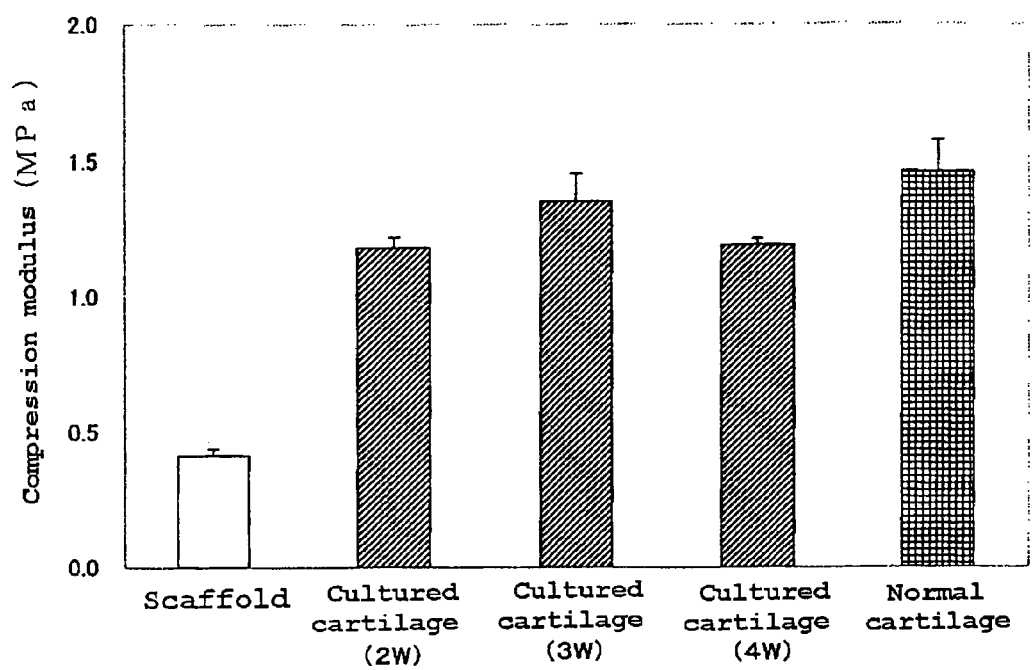
FIG. 10 represents a graph showing the result of the mechanical strength measurement of the cultured cartilage shown in Example 7.

That is, the distortion giving the stress value of $2.5\times10^{-4}$ MPa was referred to $\epsilon$ 0 (sample surface), the distortion giving the stress value of $1.5\times10^{-2}$ MPa was referred to $\epsilon$ 15, and the portions between these values were recognized as the portions subjected to pore-opening treatment. Moreover, the compression modulus was obtained from parts except for those subjected to pore-opening treatment (internal structure), and calculated from the rate of change of the compression stress between distortion increases 0.10 from $\epsilon$ 15 (FIG. 10).

The compression was carried out according to the manual of a control analysis software Texture Expert Exceed attached on "Texture analyzer TA-XT2i (product of Stable Micro Systems Ltd.)" according to ASTM: D 1621-94. In FIG. 10, "scaffold" represents one obtained by equilibrating the PLGA scaffold of Example 1-a alone by PBS, "cultured cartilage" represents the 3-dimensional cell combination of the invention, "normal cartilage" represents a goat femur cartilage, and the average value and standard deviation of each sample were plotted. Moreover, "2 W, 3 W, and 4 W" represent the cultured cartilages of the 2nd week, 3rd week, and 4th week after the start of the rotational culture, respectively.

Furthermore, an experiment using the PLGA scaffold produced by the separation method of Example 1-b was carried out in the same manner, and the equivalent result was confirmed as one obtained by a salt elution method of Example 1-a.

EXAMPLE 8

Production of a Cultured Cartilage Using a PLGA Scaffold $7.5\times10^5$ pieces of human mesenchymal stem cells (product of Biowhittaker Inc.) were cultured using DMEM medium produced by GIBCO added with 10% bovine fetal serum. After the lapse of one week, cells amplified to about 10 times were used for producing a cultured cartilage.

The PLGA scaffold produced by a salt elution method of Example 1-a and sterilized with γ-ray at 25 KGry was placed in the above medium, and deaerated under reduced pressure to spread the medium on the scaffold surface. Then, the above cultured mesenchymal stem cells (product of Biowhittaker Inc.) were seeded at the density of $1\times10^7$ cells per 1 $cm^3$ of the scaffold. The scaffold seeded with the mesenchymal stem cells was placed in a culture petri dish, said medium was added thereon to the level that the scaffold was covered, and the resultant was subjected to stand culture overnight. Thereafter, the scaffold was moved to a 10 cm-diameter culture petri dish containing 20 ml of DMEM medium produced by GIBCO (10 ng/ml TGF-β3, 50 μg/ml ascorbic acid 2-phosphoric acid, 100 μg/ml sodium pyruvate, 40 μg/ml proline, ITS-plus (Collaborative Biomedical Products), and rotational culture was carried out at the rotation rate of 30 rpm using a shaking machine capable of conducting horizontal circular motion. At the 14th day from the start of the rotational culture, the scaffold was taken out, and the produced cultured cartilage was evaluated histrogically and biochemically (ELISA).

Figure 11:
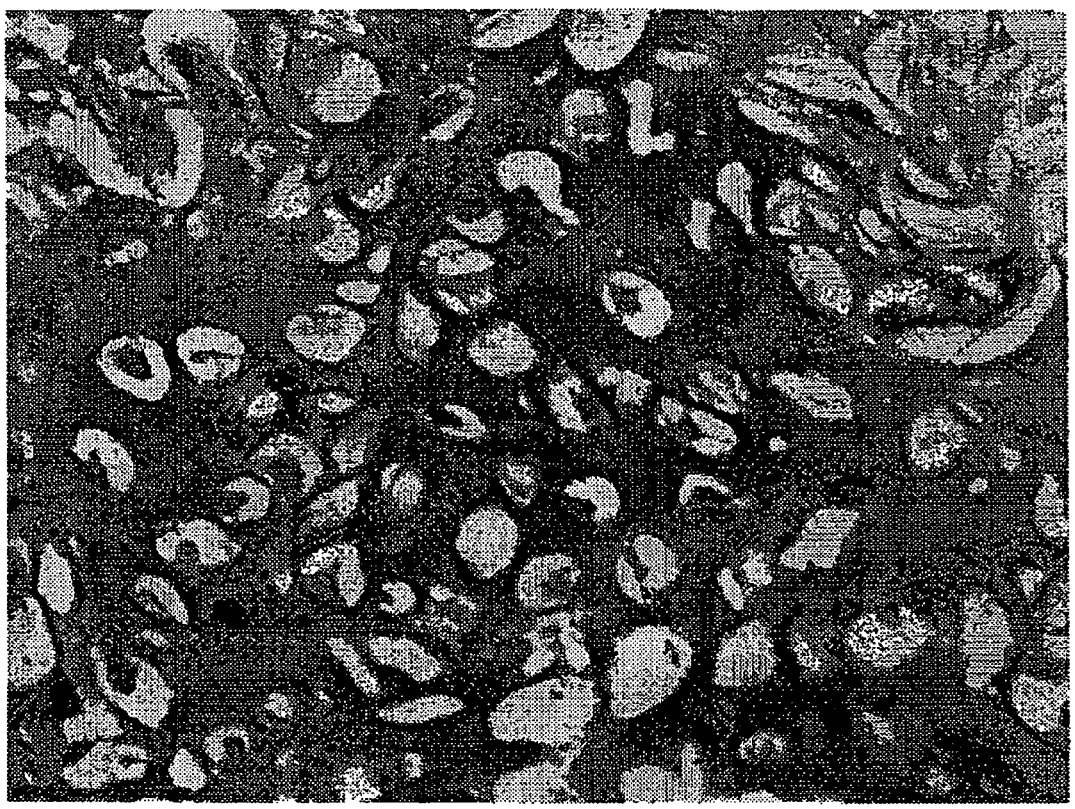
FIG. 11 shows an enlarged view of Alcian blue staining positive part of a cultured cartilage tissue.
Figure 12:
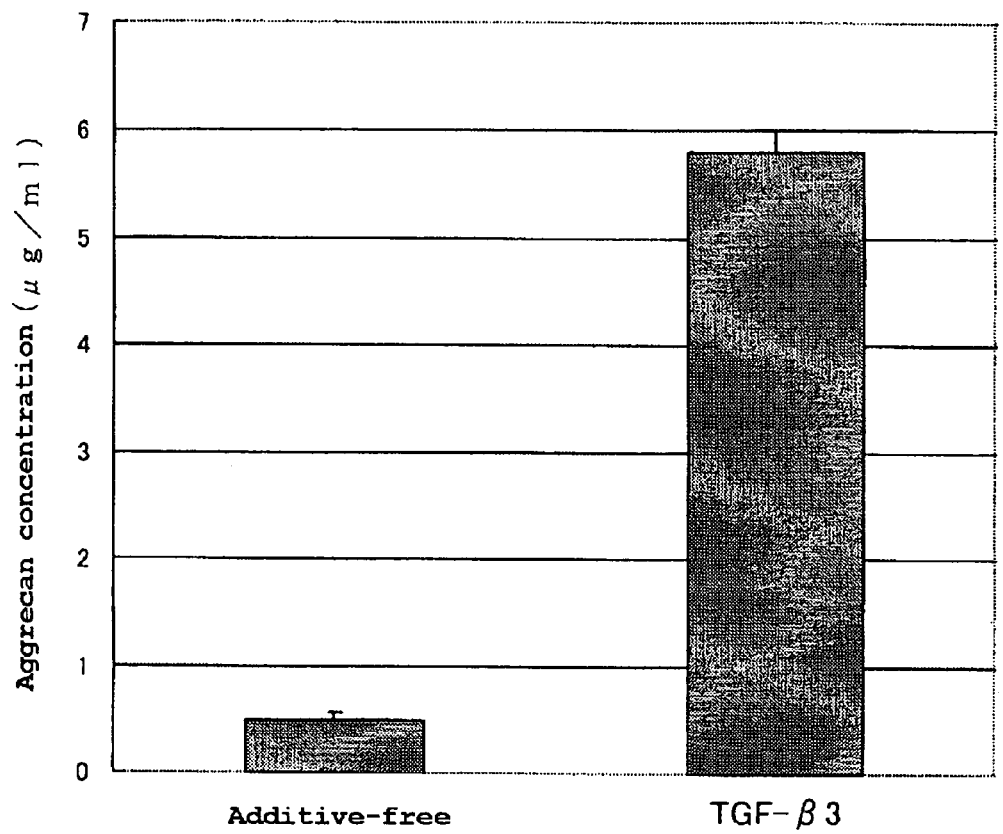
FIG. 12 shows the result of ELISA determination of cultured cartilage proteoglycan (aggrecan).
Figure 13:
FIG. 13 represents a view showing an Alcian blue staining image of a cultured cartilage tissue in a wide scope.

The tissue image of the cultured cartilage produced using this PLGA scaffold exhibited remarkable Alcian blue positivity as shown in FIG. 11. Furthermore, the cartilage cells present in these tissues did not have fibroblast shape, but had very resemble shape with permanent cartilage cells (FIG. 11). This cultured cartilage was solubilized with 4 M guanidine hydrochloric acid solution, and the detection of agrecan, which is a characteristic proteoglycan of cartilage, was attempted by ELISA. Then, the presence of agrecan was confirmed. As a comparison, a sample cultured by removing TGF-β3 from the above medium composition was produced (FIG. 12). Moreover, this PLGA scaffold has the structural characteristic of having micropore structure in which pores in one side were enlarged and pores in the other side inhibit passage of cells. In the produced cultured cartilage, polarity of tissue formation was found that Alcian blue was most positive and the form of cells was quite similar with permanent cartilage cells in the side not subjected to pore-opening treatment (pores not being enlarged), and in the side subjected to pore-opening treatment (pores being enlarged), Alcian blue staining was remained slightly weak (FIG. 13).

Furthermore, an experiment using the PLGA scaffold produced by the separation method of Example 1-b was carried out in the same manner, and the equivalent result was confirmed as one obtained by a salt elution method of Example 1-a.

EXAMPLE 9

Measurement of Mechanical Strength of a Cultured Cartilage

A cultured cartilage was produced by the method described in Example 8 using the PLGA scaffold produced by a salt elution method of Example 1-a, and made into a cultured cartilage module of 6.5 mm in diameter and 1.5 mm in thickness. This module was equilibrated in a PBS solution at 25° C.

for 30 minutes, and the stress received when the compression was applied at a head speed of 0.1 mm/second was measured by the following method.

Figure 14:
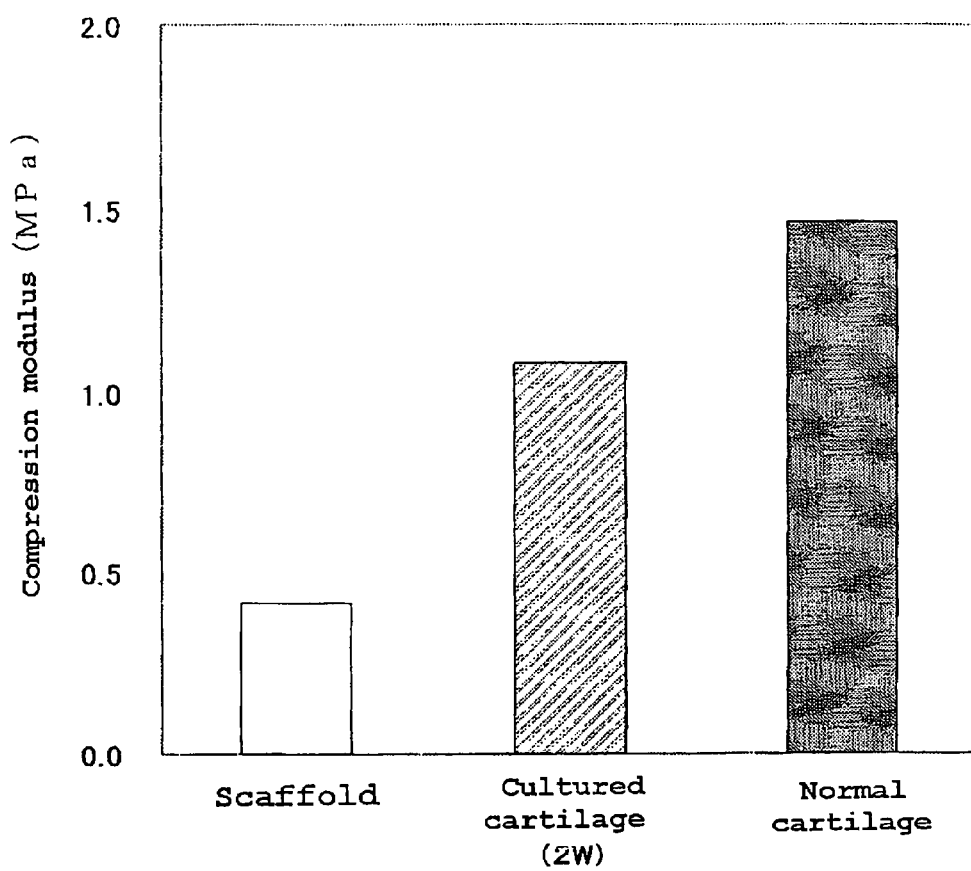
FIG. 14 represents a graph showing the result of the mechanical strength measurement of the cultured cartilage shown in Example 9.

That is, the distortion giving the stress value of $2.5 \times 10^{-4}$ MPa was referred to $\epsilon$ 0 (sample surface), the distortion giving the stress value of $1.5 \times 10^{-2}$ MPa was referred to $\epsilon$ 15, and the portions between these values were recognized as the portions subjected to pore-opening treatment. Moreover, the compression modulus was obtained from parts except for those subjected to pore-opening treatment (internal structure), and calculated from the rate of change of the compression stress between distortion increases 0.10 from $\epsilon$ 15 (FIG. 14).

The compression was carried out according to the manual of a control analysis software Texture Expert Exceed attached on "Texture analyzer TA-XT2i (product of Stable Micro Systems Ltd.)" according to ASTM: D 1621-94. In FIG. 14, "scaffold" represents one obtained by equilibrating the PLGA scaffold of Example 1-a alone by PBS, "cultured cartilage" represents the 3-dimensional cell combination of the invention, and "normal cartilage" represents a goat femur cartilage. Moreover, "2 W" represents the cultured cartilages of the 2nd week after the start of the rotational culture.

Furthermore, an experiment using the PLGA scaffold produced by the separation method of Example 1-b was carried out in the same manner, and the equivalent result was confirmed as one obtained by a salt elution method of Example 1-a.

EXAMPLE 10

Production of Cultured Bone Using a PLGA Scaffold

The PLGA scaffold produced by a salt elution method of Example 1-a and sterilized with γ-ray at 25 KGry was placed in αMEM medium containing 10% bovine fetal serum produced by GIBCO, and deaerated under reduced pressure to spread the medium on the scaffold surface. Then, MC3T3 cell, which is an osteoblast strain, was seeded at the density of $1 \times 10^7$ cells per 1 cm$^3$ of the scaffold. The scaffold seeded with the same cells was placed in a culture petri dish, said medium was added thereon to the level that the scaffold was covered, and the resultant was subjected to stand culture overnight. Thereafter, the scaffold was moved to a 10 cm-diameter culture petri dish containing 20 ml of said medium, and rotational culture was carried out at the rotation rate of 30 rpm using a shaking machine capable of conducting horizontal circular motion. At the 14th day from the start of the rotational culture, the scaffold was taken out, and the produced cultured bone was evaluated by Alizarine red staining.

Figure 15:
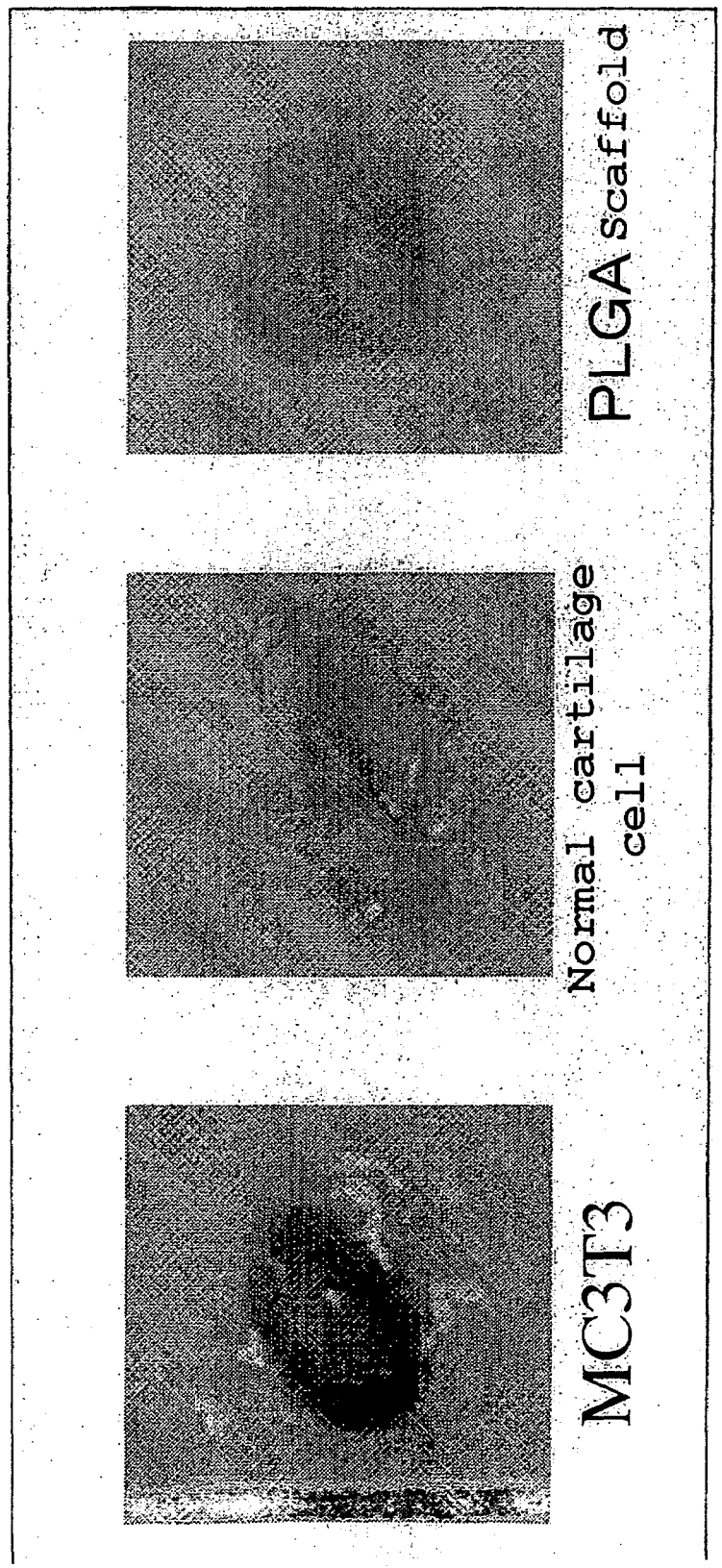
FIG. 15 represents a view showing the result of Alizarine red staining of the cultured bone shown in Example 10.

This cultured bone produced by using the PLGA scaffold exhibited Alizarine red positivity as shown in FIG. 15, and bone-like tissue was found to be formed ("MC3T3" in FIG. 15). On the other hand, one prepared by seeding the normal cartilage cells on the PLGA scaffold and culturing ("normal cartilage cell" in FIG. 15) and a PLGA scaffold not seeded with the cells ("PLGA scaffold" in FIG. 15) were not reacted with Alizarine red.

EXAMPLE 11

Treatment of Cartilage Defect in a Rabbit Using a PLGA Scaffold Seeded with a Mesenchymal Stem Cell Marrow cells were sampled from head of humerus of a Japanese white rabbit (body weight 3 to 3.5 kg, 3 to 4 month old) using a bone-marrow needle, and subjected to an initial culture for 2 to 3 weeks. The cultured cells were suspended in a medium (αMEM medium (product of GIBCO)), and prepared to be $5 \times 10^7$ cells/ml. This cell suspension was added dropwise to the pore-opened surface of a PLGA transplantation scaffold. More specifically, the PLGA scaffold produced by a salt elution method of Example 1-a and sterilized with γ-ray at 25 KGry was placed in the above medium, and deaerated under reduced pressure to spread the medium on the scaffold surface. Then, the cultured mesenchymal stem cells were seeded at the density of $1 \times 10^7$ cells per 1 cm$^3$ of the scaffold. The scaffold seeded with the mesenchymal stem cells was placed in a culture petri dish, said medium was added thereon to the level that the scaffold was covered, and the resultant was subjected to stand culture overnight.

Then, all-phase cartilage defect of about 5 mm in diameter was formed on the femoropatellar joint surface of the rabbit, and a PLGA scaffold seeded with the above cell was transplanted thereinto (seeded group). At the same time, as controls, a group consisting of only defected ones (defect group) and a group consisting of ones into which a PLGA scaffold alone was transplanted (scaffold group) were produced. After the lapse of 4 and 12 weeks from the operation, the rabbits were killed and examined macroscopically and histologically (refer to the appearances in FIGS. 16A and B, Hematoxylin-eosin (HE) and Alcian blue (AB) staining figures).

Figure 16A:
FIG. 16A represents a view showing appearance photographs of an affected part and the results of tissue staining of an affected part after the lapse of 4 weeks of treatment of cartilage defect using a PLGA scaffold seeded with a mesenchymal stem cell in a rabbit as shown in Example 11 (Hematoxylin-eosin (HE) stain, Alcian blue (AB) stain).

As a result, in the defect group, the defect parts were covered with granulation tissues both of after 4 weeks and 12 weeks. In the scaffold group, histologically, the carrier structure remains after 4 weeks, but the defect parts were repaired with fibrous tissues in which cartilage cells were scattered, and faintly stained with Alcian blue. Those of after 12 weeks from the transplantation showed the same result as the defect group. As regarding the seeded group, after 4 weeks, the defect parts were covered with cartilage-like tissues, but borders with the surroundings were confirmed. After 12 weeks from the transplantation, the defect parts were repaired with cartilage tissues without having borders with the surroundings. In the seeded group, the defect parts were repaired with cartilage cells being arranged in layers after 4 weeks from the transplantation, but staining with AB was faint. After 12 weeks from the transplantation, similarly to the surrounding normal cartilage tissues, the defect part was repaired with cartilage tissues having a complete layer structure, and also the assimilation with the surrounding tissues was preferable. Deeply-stained with AB, and quite preferable production of substrates were confirmed (FIG. 16A represents the state after 4 weeks from the operation, and FIG. 16B represents the state after 12 weeks from the operation).

In this one-side pore-opened type PLGA transplant carrier, cells could be easily seeded and transplanted with arranging in a cylindrical shape without causing cell leakage. It was considered that the transplantation maintaining this cell arrangement structure enabled cartilage regeneration near normal.

Furthermore, an experiment using the PLGA scaffold produced by the separation method of Example 1-b was carried out in the same manner, and the equivalent result was confirmed as one obtained by a salt elution method.

INDUSTRIAL APPLICABILITY

By the present invention, it becomes possible to produce a biocompatible 3-dimensional porous scaffold excellent in cell seeding ability, cell retention ability, and degree of tissue formation of cells, thus it is able to provide an excellent material for producing various living-like tissues including cartilage. Furthermore, the 3-dimensional cell combination obtainable by culturing a cell or precursor cell derived from a tissue in an artificial environment and/or the living body using this scaffold can prevent invasion of inflammatory cells in the living organ transplantation and has similar characteristics with tissues in the living body in nature of having compatibility with surrounding tissues, thus shows excellent degree of tissue formation and medical treatment effect.

The invention claimed is:

1. A 3-dimensional porous scaffold for tissue regeneration which
   comprises a structure composed of vertically long-shaped pores having a pore diameter of not less than 10 μm to not more than 500 μm and pore length of not less than 20 μm to not more than 1 cm being juxtaposedly arranged, and the spaces between the juxtaposed pores being communicated with small pores having a pore diameter of not more than 10 μm and
   which has an approximately flat plate-shape with vertically long-shaped pores in the thickness direction being juxtaposedly arranged in the surface direction, and one side face being subjected to pore-opening treatment.

2. The 3-dimensional porous scaffold according to claim 1, which is composed of a biocompatible material.

3. The 3-dimensional porous scaffold according to claim 2, wherein the biocompatible material contains at least one selected from the group consisting of polylactic acid, polyglycolic acid, lactic acid/glycolic acid copolymer, poly εcaprolactone, and lactic acid/εcaprolactone copolymer.

4. A 3-dimensional porous scaffold for tissue regeneration which comprises:
   a structure composed of vertically long-shaped pores having a pore diameter of not less than 10 μm to not more than 500 μm and pore length of not less than 20 μm to not more than 1 cm, said pores being juxtaposedly arranged, the spaces between the juxtaposed pores being communicated with small pores having a pore diameter of not more than 10 μm;
   said structure having an approximately flat plate-shape with vertically long-shaped pores in the thickness direction being juxtaposedly arranged in the surface direction, and one side face being subjected to pore-opening treatment;
   the structure being produced by a process which comprises the steps of
   a) dissolving a scaffold material in an organic solvent,
   b) dispersing a granular salt in a mold forming an approximately flat plate-shape,
   c) pouring the prepared solution into said mold, and freezing the solution at a cooling rate of not slower than 3° c/minute,
   d) drying the frozen solution in vacuum to remove the organic solvent, and
   e) removing the granular salt by washing with water.

* * * * *